United States Patent [19]

Malcolm et al.

[11] Patent Number: 5,037,411
[45] Date of Patent: Aug. 6, 1991

[54] DISPOSABLE ARTICLE MULTI-LINE CONSTRUCTION ADHESIVE

[75] Inventors: David B. Malcolm, Maplewood; William L. Bunnelle, Hugo, both of Minn.

[73] Assignee: H. B. Fuller Company, Wilmington, Del.

[21] Appl. No.: 269,157

[22] Filed: Nov. 9, 1988

[51] Int. Cl.$^5$ ............................................. A61F 13/15
[52] U.S. Cl. .................................... 604/358; 458/198; 458/284; 458/286; 458/913
[58] Field of Search ............... 428/198, 284, 286, 913; 604/358

[56] References Cited

U.S. PATENT DOCUMENTS

| | | | |
|---|---|---|---|
| 3,329,478 | 3/1966 | Harlan Jr. | 260/27 |
| 3,639,521 | 2/1972 | Haleh | 260/830 |
| 3,700,633 | 10/1972 | Wald et al. | 260/830 |
| 3,787,531 | 1/1974 | Dahlquist et al. | 260/876 |
| 3,860,003 | 1/1975 | Buell | 128/287 |
| 3,917,607 | 11/1975 | Crossland et al. | 260/28.5 |
| 3,932,327 | 1/1976 | Naylor | 260/27 |
| 3,993,613 | 11/1976 | Doss et al. | 260/27 |
| 4,050,462 | 9/1977 | Woon et al. | 128/287 |
| 4,089,824 | 5/1978 | Bronstort et al. | 260/27 |
| 4,135,699 | 1/1979 | Collins et al. | 128/290 |
| 4,147,580 | 4/1979 | Buell | 156/291 |
| 4,212,910 | 7/1980 | Taylor et al. | 428/35 |
| 4,253,461 | 3/1981 | Strickland et al. | 128/287 |
| 4,326,528 | 4/1982 | Ryan et al. | 128/287 |
| 4,392,862 | 7/1983 | Marsan et al. | 604/366 |
| 4,397,645 | 8/1983 | Buell | 604/380 |
| 4,419,494 | 12/1983 | Puletti et al. | 525/95 |
| 4,460,364 | 7/1984 | Chen et al. | 604/387 |
| 4,460,728 | 7/1984 | Schmidt Jr. et al. | 524/271 |
| 4,526,577 | 7/1985 | Schmidt Jr. et al. | 604/366 |
| 4,531,945 | 7/1985 | Allison | 604/378 |
| 4,627,847 | 12/1986 | Puletti et al. | 604/366 |
| 4,681,793 | 7/1987 | Linman et al. | 428/138 |
| 4,687,478 | 8/1987 | Van Tillburg | 604/387 |

OTHER PUBLICATIONS

Conair the Plastics Movers Brochure, "Plastics Strand Pelletizers".

Black Clawson Brochure, "Black Clawson Pelletor Underwater Pelletizing Systems".

Buss-Condux, Inc. Brochure, "Mixing and Kneading with Cuss-Kneaders".

Werner & Pfleiderer Brochure, "Plastics Technology Twin-Screw Compounding Extruder ZSK 30 for Laboratory Applications".

Werner & Pfleiderer Brochure, "Compounding Extruders for Plastics ZSK".

Welding Engineers, Inc. Brochure, "Welding Engineers Twin-Screw Extruders".

Egan Machinery Company Brochure, "Design of Extruder Screws for Extrusion Coating".

Buss-Condux, Inc. Brochure, "Buss-Kneaders® Plants for the Preparation and Pelletizing of Thermoplastics".

T. E. Sedlack, "Extruder Performance Over Broad Melt Index Ranges," Paper Synthetics Conference, 27 (1983).

H. Kuroki, "Advance in Production and Coating Technology for Hot Melt Pressure Sensitive Adhesives," 33 (1981).

P. Franz, "Continuous Compounding of Hotmelt Adhesives," 95 (1981).

B. J. Davis, "The Chemistry of $C_5$ Resins," Nippon Zeon of America Ltd. (1979).

"Machinery and Equipment," *Plastics Compounding*, 98 (1987/1988).

William H. Korcz, "Liquid Resin Injection System for Continuous Mixing of HMPSA," 81 (1981).

R. L. Adams, "Technical Aspects for Extrusion Compounding of Hot Melt Adhesives," 55 (1979).

W. N. Nissle, "Twin Screw Extruder Processing of Adhesives," 29 (179).

P. Franz, "Continuous Production of Hotmelt Adhesives, Aspects of Quality and Costing," 40 (1979).

*Primary Examiner*—James J. Bell
*Attorney, Agent, or Firm*—Merchant, Gould, Smith, Edell, Welter & Schmidt

[57] ABSTRACT

High molecular weight radial or teleblock copolymers can be used as hot melt agents in the construction of disposable laminates such as disposable diapers and feminine pads.

14 Claims, No Drawings

DISPOSABLE ARTICLE MULTI-LINE CONSTRUCTION ADHESIVE

BACKGROUND OF THE INVENTION

The present invention relates to disposable articles prepared using multi-line construction and especially to multi-line disposable diaper, sanitary napkin and bed pad constructions and to hot melt adhesives useful for the assembly thereof.

While a wide range of uses for hot melt adhesive compositions are known throughout the disposable industry, it has been found that a hot melt adhesive used for bonding in a particular use or application may be completely unsuitable for other uses or applications. Thus, various hot melt adhesive compositions have been proposed for use in the construction of disposable articles. Depending upon the type of construction employed, the adhesive must possess certain physical properties. Perhaps the most stringent properties are those required of adhesives to be used in the bonding of polyethylene films, or the like, to tissue or nonwoven substrates in the production of articles, particularly diapers, sanitary napkins and bed pads, using multi-line construction techniques. This class of disposable construction presents unique problems for the adhesive formulator. The adhesive must possess a high degree of adhesion since it is applied in the form of a number of very fine parallel longitudinal stripes thus requiring each line of adhesive to possess exceptionally high bonding properties. The adhesive must also possess sufficient adhesive and cohesive strength to provide high bond strength values when subjected to stress so the constructions cannot be easily separated. As an additional criteria, it is necessary that the adhesive, upon application, not absorb throughout the actual disposable construction and that the adhesive bonds not only remain secure but also be flexible even after the prolonged periods of storage. In addition to requiring heat and oxidation resistance on aging they must also possess sufficient bonding range and must be white or clear in color.

Initially hot melt adhesives based on ethylene vinyl acetate copolymers or on atactic polypropylene have been used for these multi-line constructions and neither of these approaches have resulted in adhesives possessing all the desirable properties discussed above. Thus, the polypropylene based adhesives have adequate adhesion requirements at the sacrifice of stability and bonding range while the ethylene vinyl acetate adhesives provide the flexibility while sacrificing adhesion and bond strength. Further, in order to formulate either type into adhesives which have the bonding range or open time required for these applications, the adhesive can be formulated as a semi-pressure sensitive adhesive which consequently has further reduced their cohesive strength resulting in loss of bonding during storage or transport at elevated temperatures.

Schmidt, U.S. Pat. No. 4,526,577 is primarily directed to hot melt adhesives based on linear A—B—A or A—B—A—B—A—B block copolymers. These adhesives contain the rubber copolymer, tackifier, oil and optional ingredients.

While the term "multi-line" construction is used herein to represent the above-described embodiment, it will be understood that the term may also be used to include articles constructed using a "multi-dot" or "multi-stripe" pattern or application, i.e. any assembly requiring the use of a large number of adhesive deposits, each deposit being of a small quantity of adhesive.

An object of the present invention is to provide a hot melt adhesive composition suitable for use in the construction of multi-line disposable articles. A further object is to provide hot melt pressure sensitive adhesive compositions which can be applied at relatively low temperatures that will retain superior bonding strength even when subjected to prolonged periods of storage.

This and other objects will be apparent from the description that follows.

SUMMARY OF THE INVENTION

We have now found that pressure sensitive hot melt compositions prepared from radial high molecular weight block copolymers (i.e. molecular weight greater than 140,000) are particularly useful in the construction of multi-line assemblies. The invention is directed to a disposable article of the multi-line type construction comprising at least one polyethylene or polypropylene substrate bonded to at least one tissue, non-woven, polyethylene or polypropylene substrate using a hot melt pressure sensitive adhesive composition comprising: (a) 5 to 15% by weight of a radial block copolymer where the B component is a polymer segment of isoprene, butadiene or hydrogenated isoprene or butadiene or mixtures thereof; (b) 40 to 80% by weight of a compatible tackifying resin; (c) 5 to 30% by weight of a plasticizing oil; (d) 0 to 5% by weight of a oil gelling agent such as a petroleum derived wax; and (e) 0.1 to 2% by weight of a stabilizer.

More particularly, the present invention is directed to the use of a hot melt adhesive composition especially adapted for the above described construction, the hot melt adhesives containing as the block copolymer a multi-block styrene-butadiene copolymer containing about 15 to 45 parts styrene per 100 parts copolymer.

DETAILED DESCRIPTION OF THE PREFERRED EMBODIMENTS

The primary component of the adhesive compositions used in the present invention are block or multi-block copolymers having the general configuration:

$(AB_n)$—Y or $(AB)_{n1}$—Y—$(B)_{n2}$ wherein the polymer blocks A are non-elastomeric polymer blocks which, as homopolymers have glass transition temperatures above 20° C., while the elastomeric polymer blocks B which can be untreated or partially or substantially hydrogenated.

The non-elastomeric blocks which make up 15 to 45% by weight of the block copolymer may comprise homopolymers or copolymers of vinyl monomers such as vinyl arenas, vinyl pyridines, vinyl halides and vinyl carboxylates, as well as acrylic monomers such as acrylonitrile, methacrylonitrile, esters of acrylic acids, etc. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred.

The elastomeric block component making up the remainder of the copolymer is butadiene or isoprene which may or may not be hydrogenated as taught, for example, in U.S. Pat. No. 3,700,633. This hydrogenation may be either partial or substantially complete. Selected conditions may be employed for example to hydrogenate the elastomeric butadiene block while not so modifying the vinyl arene polymer blocks. Other conditions may be chosen to hydrogenate substantially uniformly along the polymer chain, both the elastomeric and on-elastomeric blocks thereof being hydrogenated to practically the same extent, which may be either partial or substantially complete.

Most preferred for use herein are the radial block copolymers:

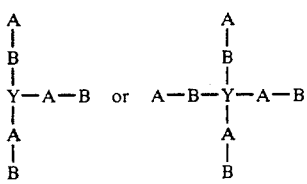

and mixtures thereof, etc., where the elastomeric block is butadiene and the non-elastomeric block is styrene and the latter is present at levels of about 20 to 40 wt-%. Block copolymers marketed commercially at this time which meet the above described requirements are available from Shell under the trade name KRATON 1184 (about 70 parts butadiene and 30 parts styrene). Blends of these high molecular weight copolymers with compatible low molecular weight block copolymers may also be employed.

A—B—A block copolymers can be used with the radial block polymers. The A blocks of such A—B—A block copolymer comprise blocks of polymerized vinyl substituted aromatic monomers and the B blocks comprise polymerized dienes having 4-12 carbon atoms. Preferably the A—B—A block copolymers are made of A blocks comprising polymerized styrene and B blocks comprising polymerized butadiene, isoprene or mixtures thereof. Such copolymers typically have a molecular weight in the range of about 70,000-140,000 and have from about 12 to 35 wt-% styrene. Such linear and multi-block copolymers are available from Shell Chemical Company, Enichem, Fina and Firestone.

We have found that the adhesive's excellent construction properties can be improved by stabilizing the oil component of the adhesive. We believe that the migration of oil from the adhesive mass to the bond line between the adhesive and a polyolefin film can cause failure of the adhesive bonds. Stabilizing the oil in the adhesive preventing its migration from the adhesive composition can increase bond strength. We have found that the bond strength can be improved using at least two mechanisms. First a gelling agent can be used which forms an emulsion contained oil gel. The gel effectively locks the oil in place within the adhesive mass, preventing its migration. Additionally, highly oil compatible tackifying agents can be used which through compatibility tend to prevent migration.

Tackifying Resin

The adhesives of the invention contain a tackifying resin in combination with a thermoplastic block copolymer and a plasticizer. Tackifying resins useful in the adhesives of the invention comprise rosin derivatives including wood rosin, tall oil, tall oil derivatives, rosin ester resins, natural and synthetic terpenes and aliphatic or mixed aliphatic-aromatic tackifying resins.

The preferred tackifying resins useful in the adhesive compositions can be hydrocarbon resins, synthetic polyterpenes, rosin esters, natural terpenes, and the like. More particularly, the useful tackifying resins include any compatible resins or mixtures thereof such as (1) natural and modified rosins such, for example, as gum rosin, wood rosin, tall oil rosin, distilled rosin, hydrogenated rosin, dimerized rosin, and polymerized rosin; (2) glycerol and pentaerythritol esters of natural and modified rosins, such, for example, as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g. styrene/terpene and alphamethyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium of a bicyclic terpene and a phenol; (6) aliphatic petroleum hydrocarbon resins having a Ball and Ring softening point of from about 70° to 135° C.; the latter resins resulting from the polymerization of monomers consisting of primarily olefins and diolefins; also included are the hydrogenated aliphatic petroleum hydrocarbon resins; (7) aromatic petroleum hydrocarbon resins and the hydrogenated derivatives thereof; and (8) alicyclic petroleum hydrocarbon resins and the hydrogenated derivatives thereof. Mixtures of two or more of the above described tackifying resins may be required for some formulations.

Aromatic monomers useful in forming the aliphatic aromatic resin compositions of this invention can be prepared from any monomer containing substantial aromatic qualities and a polymerizable unsaturated group. Typical examples of such aromatic monomers include the styrenic monomers, styrene, alphamethyl styrene, vinyl toluene, methoxy styrene, tertiary butyl styrene, chlorostyrene, etc., indene monomers including indene, methyl indene and others. Aliphatic monomers are typical natural and synthetic terpenes which contain $C_5$ and $C_6$ cyclohexyl or cyclopentyl saturated groups that can additionally contain a variety of substantial aromatic ring substituents. Aliphatic tackifying resins can be made by polymerizing a feed stream containing sufficient aliphatic monomers such that the resulting resin exhibits aliphatic characteristics. Such feed streams can contain other aliphatic unsaturated monomers such as 1,3-butadiene, cis-1,3-pentadiene, trans-1,3-pentadiene, 2-methyl-1,3-butadiene, 2-methyl-2-butene, cyclopentadiene, dicyclopentadiene, terpene monomers and others. Mixed aliphatic aromatic resins contain sufficient aromatic monomers and sufficient aliphatic monomers and optionally other $C_3$-$C_8$ unsaturated monomers to produce a resin having both aliphatic and aromatic character. The article by Davis, *The Chemistry of $C_5$ Resins*, discusses synthetic $C_5$ resin technology.

The adhesive compositions of the invention can contain rosin and rosin derivatives as a tackifying agent. Rosin is a solid material that occurs naturally in the oleo rosin of pine trees and typically is derived from the oleo resinous exudate of the living tree, from aged stumps and from tall oil produced as a by-product of kraft paper manufacture. After it is obtained rosin can be treated by hydrogenation, dehydrogenation, polymerization, esterification, and other post treatment processes. Rosin is typically classed as a gum rosin, a wood rosin, or as a tall oil rosin which indicate its source. The materials can be used unmodified, in the form of esters of polyhydric alcohols, and can be polymerized through the inherent unsaturation of the molecules. Materials are commercially available and can be blended into the adhesive compositions using standard blending techniques. Representative examples of such rosin derivatives include pentaerythritol esters of tall oil, gum rosin, wood rosin, or mixtures thereof.

Representative examples of such aliphatic resins include hydrogenated synthetic $C_9$ resins, synthetic branched and unbranched $C_5$ resins and mixtures thereof. Representative examples of such aromatic tackifying resins include styrenated terpene resins, styrenated $C_5$ resins or mixtures thereof. The selection of tackifying resins is often based on the nature of the B or midblock radial block copolymer. Rosin derivatives are best for S—I—S/S—B—S blends and can be used with either S—I—S or S—B—S alone. Hydrogenated $C_9$ or straight aliphatic resins are preferred for S—I—S copolymers. For S—B—S copolymers, styrenated terpenes or rosin esters are preferred.

Plasticizing Oils

Plasticizing oils are used in the construction attachment adhesives of the invention. Such oils are primarily hydrocarbon oils low in aromatic content. Preferably the oils are paraffinic or naphthenic in character. The oils are preferably low in volatility, are clear and have as little color and odor as possible. The use of a plasticizing oil of this invention also contemplates the use of olefin oligomers, low molecular weight polymers, vegetable oils and their derivatives and similar plasticizing liquids.

Oil Gelling or Complexing Agents

Plasticizing oils used in adhesive compositions can be prevented from migration by the use of gelling or complexing agents which tend to restrain the migration of oil through formations of gels or complexes. The oil can be restrained by a variety of gelling agents including waxes, polyethylene waxes, oxidized waxes, oxidized polyethylene waxes, polyvalent metal soaps, etc.

The following table sets forth the useful, preferred, and most preferred formulas.

TABLE 1

| Ingredient | Useful | Preferred | Most Preferred |
|---|---|---|---|
| Radial block copolymer* | 5-14 | 7-13 | 8-12 |
| A-B-A block copolymer* | 0-14 | 0-12 | 0-10 |
| Tackifier | 45-85 | 50-80 | 55-75 |
| Plasticizing oil | 5-35 | 6-30 | 8-20 |
| Synthetic polyethylene wax (or other oil complexing agent) | 0-10 | 0.1-9 | 0.25-5 |

*Total polymer content (including both radial block and linear block polymer) is typically about 15 wt - % or less of the adhesive.

In sharp contrast to prior art single stage blending procedures for the manufacture of pressure sensitive hot melt disposable article construction adhesives which are represented by Schmidt, Jr. et al, U.S. Pat. No. 4,526,577, we have found that effective commercial manufacture of the hot melt adhesives of this invention using high molecular weight radial block copolymers involves a two-step manufacturing procedure. In the first step the radial block copolymer is mixed at elevated temperature with at least one additional adhesive component such as a tackifier, plasticizers, or mixtures thereof to form a preblend or a premix wherein the block copolymer is intimately mixed with the other adhesive ingredient. The preblend is then blended with the remaining adhesive components at elevated temperature in standard commercial blending equipment.

In somewhat greater detail, from about 0.5 part of resin to about 2.5 parts of resin can be blended per part of radial block copolymer in order to form the preblend of the invention. The preblends can be prepared in conventional thermoplastic polymer processing equipment capable of providing sufficiently high shear to intimately blend the high molecular weight polymers and the low molecular weight adhesive components such as tackifying resins, oils or other low molecular weight polymeric materials or blends thereof. Examples of such equipment are single or twin screw extruders, intensive internal mixers, Mixtruders, Sigma Blade mixers and the like, which are heated to a sufficient processing temperature, typically between 250°-350° F. If a batch mixer is used the polymer is blended with the adhesive component such as resin, oil or component blends thereof, typically at an amount less than or equal to the polymer to provide a homogeneous preblend. Thereafter the remaining ingredients can be added and mixed until homogeneous.

The equipment and processes useful in the manufacture of the preblend materials of the invention is described in the following articles. The article "Machinery and Equipment" of *Plastics Compounding Redbook of 1987/88*, is a compilation of information regarding compounding and size reduction equipment including lab and production scale blending apparatus. The articles "Liquid Resin Injection System for Continuous Mixing of HMPSA" and "Extruder Performance Over Broad Melt Index Ranges" discuss blending materials having different viscosity profiles.

The article "Advance in Production and Coating Technology for Hot Melt Pressure Sensitive Adhesives—Multiruder System" discusses the multiruder system of premixer, multiruder and coater and is used for continuous production and coating of hot melt pressure sensitive adhesives for labels and tapes.

The article "Continuous Compounding of Hot Melt Adhesives" discusses continuously operating blending systems capable of blending hot melt adhesives with reduced heat history. Such compounding systems involve extrusion processing.

The article "Technical Aspects for Extrusion Compounding of Hot Melt Adhesives" discusses continuous processing systems for the manufacture of hot melt and pressure sensitive adhesive formulations using batch and twin screw manufacturing methods.

The article "Twin Screw Extruder Process of Adhesive" discusses continuous processing hot melt adhesive compounding with block polymer formulations using multi-stage feeding of oil resins, additives and base polymer.

The article "Continuous Production of Hot Melt Adhesives Aspects of Quality and Costing" discusses basic processing possibilities for producing hot melts continuously involving working from a premix and deals with four basic continuous processes. The disclosure involves multi-stage addition, pelletizing, coating, etc. Equipment for such manufacture is shown in the brochures of Welding Engineers, Inc., Eagan Manufacturing Company, Buss-Kneader, Warner and Pfleiderer, Conair and Black Clawsen. The disclosures of which relating to equipment and processing are hereby incorporated by reference herein.

We have found that for ease of handling the preblend of the invention can be divided into pieces sized for further processing. We have found that the preblend can be pelletized using a strand, waterface or underwater pelletizer (such as those made by Black Clawsen). An underwater pelletizing system can be used in which a water stream removes the cut pellet from the cutting area and directs the water-pellet stream to a centrifugal device that separates the water from the pellet and dries the pellets to a useful format.

The handling properties of the preblend pellets can be improved by treating the surface of the pellets with a nontacky organic or inorganic coating. Such coatings can comprise aqueous dispersions of water insoluble waxes, fatty acid esters, and other known anti-blocking agents. Useful inorganic anti-blocking agents can include such materials as silica, talc, gypsum, calcium oxide, magnesium oxide, etc. One mode of adding the antiblocking agent to the adhesive pellets is in the circulating water in the pelletizing machine. An addition of the antiblocking agent to the water inherently coats the pellets as they are formed at the cutting head with the antiblocking agent which remains after the pellet is separated from the water solution and dried.

The hot melt adhesive of the invention can be manufactured by pillow pelletizing, a procedure such as that disclosed in Franke, U.S. Pat. Nos. 3,723,035 and 4,054,632. The pillow-shaped pellets can be coated with a nonblocking thermoplastic coating agent. Such coating agents are known, for example EPOLENE C-10 from Eastman Chemical or AC-400 from Allied Chemical, or blends of compatible polymers and additives to control coating viscosity as required to obtain a uniform protective coat. Additionally, the preblend can be extruded in multiple ribbons onto a cooled stainless belt precoated with a compatible thermoplastic coating.

Composite Construction

Broadly, disposable composite articles such as disposable diapers, feminine protection articles, incontinent pads, bed pads and others are typically made by joining to a substrate, typically a plastic or polyolefin film substrate, an absorbent layer frequently covered by a tissue and a woven or nonwoven overlayer.

Plastic substrates useful in the articles of the invention comprise films made from polyethylene, polypropylene, polyester such as polyethylene terephthalate, polyvinyl chloride, polyvinylidine chloride, polyvinyl acetate, and other materials capable of film formation. The tissue layer is a well known, typically loosely formed cellulosic sheet of high porosity or permeability.

The woven or nonwoven layers can consist of a fluid permeable flexible material that can be made of either hydrophilic or hydrophobic fiber components. The woven and nonwoven webs comprising the fabric can comprise natural or synthetic fibers or mixtures thereof. Woven and nonwoven materials are well known and their construction methods have been practiced for many years. Woven fabrics are typically manufactured in weaving machines forming an interlocking mesh of fibers forming the layer. Nonwoven fabrics can be made through a dry laid or wet laid method in carding processes, air laid processes, or spun bond processes to produce a web that is mechanically, chemically or thermally formed. The fabric layers for use in the composite articles of the invention typically have a basis weight in the range of about 10 to 25, preferably 14 to 18 grams per square yard, a minimum dry tensile of at least 800 grams per centimeter squared in the machine direction, and at least 200 grams per centimeter squared in the cross machine direction.

Synthetic materials commonly used in forming the woven or nonwoven fabric layers include rayon, polyester, polypropylene, polyethylene, nylon and others.

Absorbent layers bonded into the disposable articles of the invention by the adhesive of the invention comprise typically cellulosic pulp or fluff, super-absorbent batts or combinations of fluff and super-absorbent materials. Such fluff layers are often formed and wrapped in tissue to provide mechanical integrity to the fluff which has little inherent mechanical strength. Fluff is typically manufactured through the formation of finely divided cellulosic fibers, however other materials can be used to form highly absorbent fluff or pulp layers.

In the continuous manufacture of the disposable articles of this invention and particularly disposable diapers, a small amount of adhesive in the multi-line, multi-dot, fine line, or random pattern is applied by extrusion, wheel or spray application to a thin plastic film substrate. The application occurs at a temperature of about 250°-325° F. and the adhesive is applied at a rate of about 0.1 to 2 mg/lineal inch. The absorbent materials forming the absorbing inner liner of the disposable article is applied to the multi-line adhesive on the film substrate.

In somewhat greater detail, disposable diapers are made in a continuous process by adhering the components of the disposable diaper to a continuous polyethylene or polypropylene film sheet from which the diaper is cut after the individual components are adhered. Typically the components are added in stages including an addition of the absorbent layer and the optional addition of a waist shield.

In such a technique, thin lines of adhesive are extruded onto the material at a rate of about 0.1 to 2 milligrams per lineal inch of adhesive and the absorbent layers are bonded to the fine lines of adhesive. Such application can be in the form of multi-lines, multi-dots, or other adhesive pattern that can be effectively formed on the poly surface of the film for construction purposes. The absorbent layer is laid down on a continuous web of the poly film. After the components are assembled the individual diapers are cut from the continuous web. Preferably the leg openings are cut with a water jet spray, while the individual diapers are cut with a rotary knife.

Optionally, a waste barrier can be formed in the diaper waist area by adhering a polyethylene film layer over the fluff or absorbent layer at the cut forming the waist band. The adhesive is typically applied at the bond between the poly waste shield and the poly backing, forming an overlapping layer that prevents wicking from the absorbent layer past the waist band to the exterior of the diaper.

Test Procedures

The following test procedures were used to test the Examples that follow the procedures.

A. Dynamic Peel and Static Shear Tests for Multibead Adhesives

Scope:
Static Shear:
This test is an indication of an adhesive's ability to withstand bond failure under a constant load at a temperature approximating the use temperature of a disposable article.

Dynamic Peel:
This test is used to determine the bonding strength of an adhesive when subjected to a dynamic peel force.

Materials and Equipment:
1. Multibead applicator similar to Meltex CT-225 having adjustable temperature, web speed, application rate and nip pressure.
2. Suitable force measuring device (i.e., Instron or I-Mass).
3. Programmable oven capable of maintaining 37° C. (100° F.) for 8 hours and registering failure times.
4. 50 gram mass equipped with mechanical means of attaching to samples.
5. Release paper cut into 2"×8" strips.
6. Nonwoven fabric and polyethylene film.

Procedure:
Adjust multibead applicator to proper settings. Preferred settings are shown below. Adjustments can be made based on the type of adhesive or application. Normally, beads should be applied to the treated side of the poly and nipped to the nonwoven or other substrate.

Preferred Multibead Settings:

| | |
|---|---|
| Temperature | 275° F., 300° F. |
| Nip Pressure | 1.4 bar (20 psi). |
| Application Rate | 1.6 mg/inch/bead |
| Swivel Roll | Applied, but no pressure |
| Rewind and Unwind Tension | As low as possible |
| Web Speed | 45 ± 5 meters/min. |

Use the following equation to determine either flow rate or web speed.

$$\text{flow rate (g/min)} = \frac{\text{(web speed (39.4 (App. (M/min)) (in/M)) rate)}}{(g/in/bd)(\# \text{ of beads})}$$

Run several meters of good application at 1.6 mg/inch/bead coat weight. During the run, drop in 8–10 strips of release paper. Make sure they are applied as straight across the bead as possible.

1. Procedure for static shear:

A. Sample preparation—mark along the bond line at 1 inch intervals. Cut across 3 bond lines at these intervals. Cut off the PE at one end and NW at the other end resulting in a typical shear sample. Prepare 7-8 samples.

B. Test procedure—preheat oven to 100° F. Preclamp all samples to be tested to a 50 gram mass. Hang all samples in oven as quickly as possible. Take care to insure that all samples hang freely and do not interfere with each other. Close oven, note starting time, and record failure times.

2. Procedure for Dynamic Peel:

A. Sample preparation—cut across the bond lines in the middle of the release paper. Then cut out about 3 inches of a 1 inch wide strip containing 1 bead. The resulting strip should have 1 inch of release paper and 2 inches of a single bead. Prepare 7-8 samples.

B. Test procedure—run T-peels on 7-8 samples at room temperature using a crosshead speed of 1 in/min., 25 seconds dwell time. Start crosshead and run for 10 seconds and then reset the counter for 25 more seconds. Use this average for the peel value.

Report:
1. Static shear:
Average elapsed hang time (in minutes).
Failure mode (adhesive vs. substrates).
Additional descriptive statistics and pertinent information such as adhesive I.D., application temperature, nip pressure, application rate.

Samples that sustain 480 minutes of loading should be recorded as such and noted as "did not fail".

2. Dynamic Peel:
Average maximum force to rupture (in grams).
Failure mode (adhesive, substrate or cohesive).
Additional descriptive statistics and pertinent information as described above.

COMPARATIVE EXAMPLE A

Using standard hot melt processing technology, the following multi-line adhesive was prepared from Schmidt, U.S. Pat. No. 4,526,557.

TABLE 1

| Ingredient | Name | Percent |
|---|---|---|
| Multiblock A-B-A-B-A-B block copolymer | STEREON 840A | 20.0 |
| Tackifier | ZONATAC 105 LITE | 60.0 |
| Plasticizing oil | White USP Mineral Oil | 20.0 |
| Antioxidant | IRGANOX 1010 | 0.1 |

The adhesives of Table 4, No. 1, Comparative Example A were tested for viscosity, color, static shear, softening point, SAFT and creep resistance at 100° F. The results of that testing is shown in the following table.

TABLE 2

| | Example A | Adhesive of Table 4, No. 1 |
|---|---|---|
| Brookfield Viscosity spindle SC4-21 | | |
| at 250° F. | 11,240 cP | 12,700 cP |
| at 275° F. | 5,430 cP | 6,300 cP |
| at 300° F. | 2,970 cP | 3,150 cP |
| at 325° F. | 1,768 cP | 1,875 cP |
| at 350° F. | 1,170 cP | 1,200 cP |
| Gardner Color | 2-3 | 3-4 |
| Multiline Static Shears at 100° F. | 143 min. | 326 min. |
| Mettler Soft. Pt. | 170° F. | 187° F. |
| SAFT | 146° F. | 165° F. |
| Peel test* | 105/110° F. | 110/115° F. |
| Dynamic Peel Adhesion | Cohesive failure (123 gms) | Substrate failure |

*(Pass/Fail, see Schmidt, U.S. Pat. No. 4,526,577 Crossmachine direction.) Bonds were made on a Meltex CT-225 according to procedures outlined in the static shear test method at a coat weight of 1.6 g/min.

The data recorded in Table 2 comparing a standard adhesive (Comparative Example A) with the adhesive of Table 4, No. 1 of the invention shows that the invention in comparison to the Comparative Example provides superior multi-line construction properties. Further, with respect to the multi-line construction properties of the adhesives, applicant's adhesive is a significant improvement over the multi-line adhesive disclosed in the Schmidt patent. The multi-line static shear test indicates that the multi-line bond between the polyethylene film and nonwoven has a much greater resistance to shear at body temperature, indicating that the disposable article made with the adhesive of the invention would be much more likely to retain its mechanical integrity while worn. The dynamic peel adhesion test indicates that the Schmidt adhesive bond between nonwoven and polyethylene is subject to adhesive failure, while the adhesive of the invention maintains the integrity of the bond until the substrate itself fails with no cohesive failure noted. The peel test shows some superiority to the Schmidt materials.

EXAMPLE I

In a Baker-Perkins twin screw 80 millimeter compounder extruder having 2 feed ports and maintained at 275° F., approximately equal volumes of radial block copolymer (KRATON D 1184) and tackifying resin (ZONATAC 105) were blended using established extrusion processing techniques as described in "Continuous Production of Hot Melt Adhesives, Aspects of Quality and Coating", at a rate of 300 lbs. per hour by adding the copolymer and a portion of resin to a feed port and the remaining resin through a second feed port. The blended rubber/resin mixture is extruded through a three die section with multiple circular ports and is pelletized under 50° F. water. The pelletized preblend is treated with an aqueous talc dispersion (about 1 wt-% in water) to reduce blocking.

EXAMPLE II

Example I was repeated except that the pellets are dusted with talc to reduce blocking at a weight add-on of about 0.07 wt-% talc.

EXAMPLE III

In a Baker-Perkins twin screw compound extruder having two feed ports and a single screw side stuffer at 275° F. at 300 lbs. per hour manufacturing rate, an adhesive preblend of the following composition is made:

TABLE 3

| Ingredient | Preblend I Name | Parts (Wt.) |
|---|---|---|
| Radial block polymer | K 1184 | 1 |
| Tackifier | ZONATAC 105 | 1.5 |

The composition was pelletized in 90° F. water containing approximately 1 wt-% talc resulting in a talc coating add-on of about 0.07 wt-%.

Into a heated sigma blade mixer was placed 19.6 parts of TUFFLO 6056 oil, 0.5 parts of WESTON 619 antioxidant and 26.0 parts of Preblend I. The contents of the mixer were agitated until uniform and into the mixer was placed 53.3 parts of the tackifying resin (PERMALYN 305). This adhesive is shown as No. 1 in Table 4.

The following Table 4 sets forth adhesives and test results comparing the adhesives of the invention to adhesives of the prior art based on STEREON 840A and KRATON 1111 and 1102 polymer.

TABLE 4

|  | 1 | 2 | 3 | 4 | 5 | 6 | 7 | 8 | 9 | 10 | 11 | 12 |
|---|---|---|---|---|---|---|---|---|---|---|---|---|
| KRATON D-1184 | 9.5 | 10.64 |  |  |  | 20.0 |  |  |  |  |  |  |
| STEREON 840 A |  |  | 10.0 |  |  |  | 20.0 |  |  | 30.0 |  |  |
| KRATON 1102 |  |  |  | 10.0 |  |  |  | 20.0 |  |  | 30.0 |  |
| KRATON 1111 |  |  |  |  | 10.0 |  |  |  | 20.0 |  |  | 30.0 |
| PERMALYN 305 | 51.9 | 53.3 | 54.5 | 54.5 | 54.5 | 44.5 | 44.5 | 44.5 | 44.5 | 34.5 | 34.5 | 34.5 |
| ZONATAC 501 | 14.3 | 15.96 | 15.0 | 15.0 | 15.0 | 15.0 | 15.0 | 15.0 | 15.0 | 15.0 | 15.0 | 15.0 |
| WESTON 619 | 0.5 | 0.5 |  |  |  |  |  |  |  |  |  |  |
| IRGANOX 1076 |  |  | 0.5 | 0.5 | 0.5 | 0.5 | 0.5 | 0.5 | 0.5 | 0.5 | 0.5 | 0.5 |
| TUFFLO 6056 | 19.0 | 19.6 | 20.0 | 20.0 | 20.0 | 20.0 | 20.0 | 20.0 | 20.0 | 20.0 | 20.0 | 20.0 |
| PETROLITE E-1040 | 4.8 |  |  |  |  |  |  |  |  |  |  |  |
| Visc. cP at 275° F. | 6,300 | 8,350 | 950 | 1,125 | 1,188 | 186,000 | 4,250 | 6,250 | 6,200 | 16,400 | 20,000 | 25,200 |
| Dynamic peel adhesion | SSF | SSF | CF 69 gm | CF 44 gm | CF 32 gm |  | SSF | SSF | SSF | AFN 49 gm | AFN 14 gm | AFP 27 gm |
| Static shear at 100° F. (min.) | 326 | 161 | 136 | 28 | 75 |  | 84 | 128 | 176 | 49 | 219 | 509 |

SSF = Substrate failure
CF = Cohesive failure
AFN = Adhesive failure to nonwoven
AFP = Adhesive failure to polyethylene Table 4 compares adhesives prepared with KRATON D 1184, a preferred high molecular weight radial block copolymer of the invention and comparison adhesives prepared from STEREON 840A (a linear multi-block A—B—A—B—A—B copolymer), KRATON 1102, and KRATON 1111 (two linear A—B—A block copolymers). The adhesives are compared at amounts ranging from about 10 to about 30 parts of polymer per about 100 parts of adhesives. These data clearly show that the adhesives made with 15 wt-% and less of KRA- TON D1184 are different and superior to conventional adhesives with 15 wt-% polymer in adhesive properties. These superior properties are obtained from a polymer with a substantially different function, at substantially differing proportions to provide substantially different test results.

The high molecular weight radial block copolymers of the invention function substantially differently than the polymers disclosed in the Schmidt patent. The Schmidt polymers are low molecular weight polymers having a molecular weight of less than 140,000 and the Schmidt patent is primarily directed to the linear A—B—A and A—B—A—B—A—B block copolymer. These differences between the high molecular weight radial block copolymers of the invention and the polymers of the Schmidt application result in the use of substantially reduced proportions of polymer that surprisingly give results that are superior to the Schmidt adhesives in a multi-line construction mode.

In the dynamic peel adhesion test, adhesives prepared using the linear block copolymers of the Schmidt patent provide adequate properties only at amounts of the polymer that approximate 20 wt-%. At lesser proportions the adhesive fails cohesively. At greater proportions (i.e., 30 wt-%), the adhesive fails adhesively at either the nonwoven or the polyethylene backing sheet. In sharp contrast, the adhesive of the invention using the high molecular weight radial block copolymers at amounts resulting in cohesive failure in the adhesives of the invention produce an adhesive bond stronger than the substrate which adhesive does not fail at test conditions.

We have shown in the above discussion and tables of data that the adhesive of this invention is a superior multi-line construction adhesive.

TABLE 5

|  | 1 | 2 |
|---|---|---|
| KRATON 1184 | 9.12 | 9.12 |
| KRATON 1117 | 4.9 | 4.9 |
| ZONATAC 501 | 13.18 | 13.18 |
| KAYDOL MINERAL OIL | 19.4 | 19.4 |
| WESTON 619 | 0.5 | 0.5 |
| PERMALYN 305 | 47.9 | 49.9 |
| AC-9 | 5.0 |  |
| PETROLYTE E-1040 |  | 3.0 |
| Creep resistance 4 hrs. at 100° F. | 3.0% | 11.4% |
| Static shear at 100° F. | 275 min. | 260 min. |
| Viscosity at 275° F. | 12,875 cP | 9,325 cP |
| Storage at 140° F. | No change | No change |
| Dynamic Peel Adhesion | SSF | SSF |

SSF = Substrate failure
CF = Cohesive failure

Table 5 shows that the use of other block copolymers in combination with a high molecular weight radial polymer will result in adhesive with improved properties over the prior art.

In view of the disclosure and data in this case and particularly in view of Tables 2, 4 and 5, we have shown that the adhesive compositions of this invention are prepared from polymers having substantially different functions than that disclosed in the Schmidt and Puletti patents. Further the adhesive properties are obtained in a substantially different way, i.e. with different proportions. Lastly, the resulting properties are substantially different in that the adhesives of the invention are superior to the Schmidt materials in construction properties and possess properties not present in the Schmidt adhesives.

The above discussion provides a basis for understanding the spirit and scope of the invention. However, since many embodiments of the invention can be made obtaining the benefits of the invention, the invention resides in the claims hereinafter appended.

We claim:

1. A disposable article of the multi-line construction comprising at least one polyethylene or polypropylene substrate bonded to at least one tissue, non-woven, polyethylene or polypropylene substrate using a hot melt pressure sensitive adhesive composition comprising:

(a) 5 to 15% by weight of a radial copolymer having the formula:

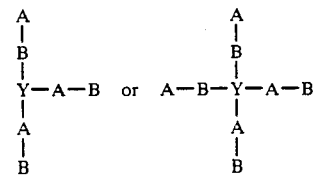

having a molecular weight greater than 140,000 containing at least 15 parts styrene per 100 parts where polymer blocks A are styrene blocks and polymer block B is butadiene or hydrogenated butadiene;

(b) 40 to 80% by weight of a compatible tackifying resin;

(c) 5 to 30% by weight of a plasticizing oil;

(d) 0 to 5% by weight of a petroleum derived wax; and (e) 0.1 to 2% by weight of a stabilizer.

2. The disposable article of claim 1 wherein the tackifying resin is any compatible resin or mixture thereof selected from the group consisting of: (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C.; (5) phenolic modified terpene resins and hydrogenated derivative thereof; (6) aliphatic petroleum hydrocarbon resins having a ball and ring softening point of from about 70° to 130° C.; (7) aromatic petroleum hydrocarbon resins and the hydrogenated derivatives thereof; and (8) alicyclic petroleum hydrocarbon resins and the hydrogenated derivatives thereof.

3. The disposable article of claim 1 selected from the group consisting of sanitary napkins and bed pads.

4. A disposable article of the multi-line type construction comprising at least one polyethylene or polypropylene substrate bonded to at least one tissue, non-woven, polyethylene or polypropylene substrate using a hot melt pressure sensitive adhesive composition comprising:

(a) 5 to 15% by weight of a radial block copolymer having the formula:

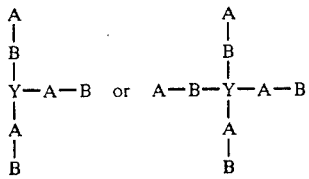

having a molecular weight greater than 140,000 wherein the A component is styrene and the B component is butadiene and wherein the styrene component is present in an amount of about 15 to 45 parts per 100 parts of the copolymer;

(b) 40 to 80% by weight of a compatible tackifying resin;

(c) 5 to 30% by weight of a plasticizing oil;

(d) 0 to 5% of weight of a petroleum derived wax; and (e) 0.1 to 2% by weight of a stabilizer.

5. The disposable article of claim 4 wherein the block copolymer comprises 57 parts butadiene and 43 parts styrene.

6. The disposable article of claim 4 wherein the tackifying resin is any compatible resin or mixture thereof selected from the group consisting of (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C.; (5) phenolic modified terpene resins and hydrogenated derivatives thereof; (6) aliphatic petroleum hydrocarbon resins having a ball and ring softening point of from about 70° to 135° C.; (7) aromatic petroleum hydrocarbon resins and the hydrogenated derivatives thereof; and (8) alicyclic petroleum hydrocarbon resins and the hydrogenated derivatives thereof.

7. The disposable article of claim 6 wherein the tackifying resin is a modified terpene resin having a ring and ball softening point of about 100°–120° C.

8. The disposable article of claim 6 wherein the tackifying resin is an aromatic petroleum hydrocarbon resin or hydrogenated derivative thereof.

9. The disposable article of claim 4 selected from the group consisting of sanitary napkins and bed pads.

10. A disposable diaper produced using a multi-line type construction comprising at least one polyethylene or polypropylene substrate bonded to at least one tissue, non-woven, polyethylene or polypropylene substrate using a hot melt pressure sensitive adhesive composition comprising:

(a) 5 to 15% by weight of a radial copolymer having the formula:

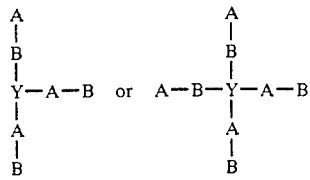

having a molecular weight of about 140,000 wherein the A component is styrene and the B component is butadiene and wherein the styrene components is present in an amount of about 15 to 45 parts per 100 parts of the copolymer;

(b) about 40 to 80% by weight of a compatible tackifying resin;

(c) 5 to 30% by weight of a plasticizing oil;

(d) 0 to 5% by weight of a petroleum derived wax; and (e) 0.1 to 2% by weight of a stabilizer.

11. The disposable diaper of claim 10 wherein the block copolymer comprises about 70 parts butadiene and 30 parts styrene.

12. The disposable article of claim 10 wherein the tackifying resin is any compatible resin or mixture thereof selected from the group consisting of (1) natural and modified rosins; (2) glycerol and pentaerythritol esters of natural and modified rosins; (3) copolymers and terpolymers of natured terpenes; (4) polyterpene resins having a softening point, as determined by ASTM method E28-58T, of from about 80° to 150° C.; (5) phenolic modified terpene resins and hydrogenated derivatives thereof; (6) aliphatic petroleum hydrocarbon resins having a ball and ring softening point of from about 70° to 135° C.; (7) aromatic petroleum hydrocarbon resins and the hydrogenated derivatives thereof; and (8) alicyclic petroleum hydrocarbon resins and the hydrogenated derivatives thereof.

13. The disposable article of claim 12 wherein the tackifying resin is a modified terpene resin having a ring and ball softening point of about 100°–120°.

14. The disposable article of claim 12 wherein the tackifying resin is an aromatic petroleum hydrocarbon resin or hydrogenated derivative thereof.

* * * * *